(12) United States Patent
Yeh

(10) Patent No.: US 6,989,246 B2
(45) Date of Patent: Jan. 24, 2006

(54) SENSOR FORMULATION FOR SIMULTANEOUSLY MONITORING AT LEAST TWO COMPONENTS OF A GAS COMPOSITION

(75) Inventor: Ming-Hsiung Yeh, New Freedom, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 592 days.

(21) Appl. No.: 10/041,661

(22) Filed: Jan. 10, 2002

(65) Prior Publication Data

US 2003/0133123 A1 Jul. 17, 2003

(51) Int. Cl.
*C12Q 1/04* (2006.01)

(52) U.S. Cl. .......................................... 435/34; 435/31
(58) Field of Classification Search .................. 435/34, 435/29, 31, 287.4, 287.5, 287.9, 807, 288.7; 422/79, 82.08; 204/431
See application file for complete search history.

(56) References Cited

U.S. PATENT DOCUMENTS

| | | | |
|---|---|---|---|
| 4,752,447 A | | 6/1988 | Kimmel et al. |
| 4,785,814 A | | 11/1988 | Kane .......................... 128/634 |
| 4,824,789 A | * | 4/1989 | Yafuso et al. .................. 436/68 |
| 4,863,694 A | | 9/1989 | Kimmel et al. |
| 5,019,350 A | | 5/1991 | Rhum et al. ................ 422/8.07 |
| 5,266,271 A | * | 11/1993 | Bankert et al. ........... 422/82.07 |
| 5,326,585 A | * | 7/1994 | Nelson et al. ............ 427/163.2 |
| 5,489,988 A | | 2/1996 | Ackley et al. |
| 5,517,313 A | | 5/1996 | Colvin, Jr. |
| 5,567,598 A | | 10/1996 | Stitt et al. |
| 5,629,533 A | | 5/1997 | Ackley et al. |
| 5,747,349 A | | 5/1998 | van den Engh et al. .... 436/172 |
| 5,852,126 A | * | 12/1998 | Barnard et al. ........... 525/326.3 |
| 6,080,574 A | * | 6/2000 | Berndt ..................... 435/288.7 |
| 6,230,545 B1 | * | 5/2001 | Adolph et al. .............. 73/31.05 |
| 6,241,948 B1 | | 6/2001 | Watkins et al. |
| 6,254,831 B1 | * | 7/2001 | Barnard et al. ........... 422/82.08 |
| 6,368,558 B1 | * | 4/2002 | Suslick et al. ................. 422/55 |
| 6,395,506 B1 | * | 5/2002 | Pitner et al. ................... 435/32 |

FOREIGN PATENT DOCUMENTS

EP    0 105 870    10/1982

OTHER PUBLICATIONS

Dourado, S. Development of Fluorescent Fiber Optic . . . SPIE Conference vol. 3540, Nov. 1998.*
Ferguson, J. Simultaneous Monitoring of pH, CO2 and O2 Using an Optical Imaging Fiber. Analytica Chimica Acta 340(1–3)123–131, 1997.*

* cited by examiner

*Primary Examiner*—Ralph Gitomer

(57) ABSTRACT

The present invention is directed to a sensor system for monitoring metabolic activity of an anaerobic or aerobic microorganism. The present invention further relates to a sensor system that can individually and simultaneously monitor oxygen and carbon dioxide levels of a gas composition. Also provided is a sensor formulation for use with the sensor system of the present invention and a method of making the same.

11 Claims, 2 Drawing Sheets

SENSOR FORMULATION FOR SIMULTANEOUSLY MONITORING AT LEAST TWO COMPONENTS OF A GAS COMPOSITION

BACKGROUND OF THE INVENTION

Microorganisms pervade our environment affecting our lives in both beneficial and harmful ways. For this reason there is an ever increasing requirement to provide a sensitive, effective, speedy mechanism for the detection, identification and study of the presence and metabolic activity of microorganisms.

In recent years the science of microbiology has experienced considerable advancements. This is particularly true for the field of sensors used in the detection, identification and analysis of the behavior of microorganisms. While progress has been made in the field of monitoring microorganisms, inefficiencies in the commonly used monitoring methods still exist. For example, a slow but effective procedure for antimicrobic susceptibility testing, the Bauer-Kirby Disc Method, is still used in hospital environments. This method uses the presence or absence of visible growth of the microorganisms to indicate the efficacy of an antimicrobic compound, and generally requires an 18 to 24 hour incubation period to allow for microorganism growth before a result can be obtained.

Another popular method for antimicrobic susceptibility testing is the broth micro-dilution method, such as the Sceptor RTM. System for identification and antimicrobic susceptibility testing of organisms (Becton Dickinson Diagnostic Instrumentation Systems, Sparks, Md.). That system uses a disposable plastic panel having a plurality of low volume cupulas (ca. 0.4 ml per cupula), each containing a different test compound or a different concentration of a test compound dried on the cupula surface. The organism to be tested is suspended in the desired testing medium, and aliquots are delivered to the individual cupulas of the test panel. The reagent dried on the panel dissolves in the sample, and the system is then incubated overnight (18 to 24 hrs.) to allow sufficient time for the organisms to interact with the reagent and for visible growth to appear. The panel is subsequently examined visually for the presence or absence of growth, thereby obtaining information on the susceptibility of the organism undergoing testing. Additional wells aid in identifying the organism. However, this test method, like the Bauer-Kirby Disc Method, suffers from the drawback of also requiring a long incubation period.

In recent years efforts have been made to avoid the long incubation times required for the above discussed monitoring methods. These innovations have focused on the monitoring of metabolic activity of microorganisms rather than monitoring the growth of colonies. Many approaches to monitoring metabolic activity of microorganisms have been reported in the attempt to rapidly and accurately monitor such metabolic activity.

One innovation in the field of microorganism monitoring is an apparatus, which utilizes light scattering optical means to determine susceptibility by probing the change in size or number of microorganisms in the presence of various antimicrobic compounds. An example of commercial instruments, which utilize this methodology is embodied by the Vitec System (BioMerieux Corp.). At best this system is expected to yield information on antimicrobic susceptibility of microorganisms within 6 hours for many organism and drug combinations. Other combinations can require as long as 18 hours before the antimicrobic susceptibility of the organism can be determined by the Vitech System method.

In an effort to improve on the Bauer-Kirby procedure, modifications have been developed which allow certain samples to be read in four to six hours. However, this modified system is destructive in nature, requiring the spraying of a developing solution of a color forming dye onto the test plate. The destructive effect of the developing solution prohibits re-incubation and reading at a later time if the initial rapid technique fails. Thus, the experiment cannot be continued for a standard evaluation at a later time.

Still other approaches have involved monitoring of microbial oxygen consumption by the measurement of pH and/or hemoglobin color change, or by the use of dyes such as triphenyl-tetrazolium chloride and resazurin, that change color in response to the total redox potential of the liquid test medium.

The monitoring of the consumption of dissolved oxygen by microorganisms, as a marker of their metabolism, has been studied for many years. For example, C. E. Clifton monitored the oxygen consumption of microorganisms over a period of several days using a Warburg flask in 1937. This method measured the change in oxygen concentration in a slow and cumbersome manner.

The "Clark" electrode, an electrochemical device, is also commonly used to measure dissolved oxygen. Unfortunately, the Clark electrode consumes oxygen during use (thereby reducing the oxygen available to the microorganisms) and the "standard" size electrode is typically used only to measure volumes of 100 mls or greater to prevent the electrode from interfering with the measurements.

A "miniature" Clark electrode has been described, but this electrode is a complicated multi-component part, which, like the larger electrode, must be in contact with the solution being measured. While an oxygen permeable membrane can be used to prevent the electrode components of the device from interacting with the constituents of the test solution, the oxygen must still equilibrate between the test solution and the measurement system and is consumed once it passes the membrane.

Optical systems which can yield oxygen concentration data, have been developed to overcome the shortcomings of the Clark electrode systems. The main advantage of such optical methods is that the instrumentation required to determine quantitative value does not itself make physical contact with the test solution. Optical techniques allowing both calorimetric and fluorometric analyses for oxygen to be carried out rapidly and reproducibly are known, and costs for such analyses are often quite low. For example, several luminescent techniques for the determination of oxygen have been described which are based on the ability of oxygen to quench the fluorescence or phosphorescence emissions of a variety of compounds. However, such methods have not been readily adapted to microbial monitoring. Further, such systems, like the Clarke Electrode system are limited to monitoring only the consumption of dissolved oxygen by microorganisms.

Other systems have been described that provide information on the presence, identity and antimicrobic susceptibility of microorganisms in a period of eight hours or less. Wilkins and Stones in U.S. Pat. No. 4,200,493 disclose a system that uses electrodes and a high impedance potentiometer to determine the presence of microorganisms. In U.S. Pat. No. 3,907,646 Wilkins et al disclose an analytical method which utilizes the pressure changes in the headspace over a flask associated with microbial growth for the detection and surveillance of the organisms. U.S. Pat. No. 4,220,715 to Ahnell, discloses a system wherein the head space gas above a test sample is passed through an external oxygen detector for determination of the presence of microorganisms. Ahnell, in U.S. Pat. No. 4,152,213, discloses a system for analysis by monitoring the vacuum produced by growing organisms in a closed head space above a test sample. U.S. Pat. No. 4,116,775 to Charles et. al is an example of the use of optical means based on the increase in turbidity or optical density of a growing microbial culture for the detection and monitoring of bacterial growth. As with the Clarke Electrode systems, these systems are designed to provide data limited to oxygen consumption.

U.S. Pat. No. 5,629,533 issued to Ackley et al. is exemplary of optical sensors, which have been developed for monitoring carbon dioxide levels on a continuous basis. Such sensors involve the use of glass fiber optics in combination with a sol-gel sensor element, which contains a chemical indicator sensitive to the presence of carbon dioxide. This system encompasses a grooved substrate with a sol-gel material having a chemical indicator adhered within the grooves. Fiber optic cables are coupled to the grooves and as light is passed through the fiber optic cables, the transmission is affected by the sol-gel sensor element.

While testing methods as exemplified above have improved in recent years to provide faster more accurate means of detecting the growth and metabolic activity of microorganisms, it is a common shortcoming of such testing methods that none of the innovations have provided a biological sensor that is capable of simultaneously detecting growth of both anerobic and aerobic microorganisms in a sample. This limitation in commonly used monitoring systems exists because such systems typically allow only one gas component to be detected in one sensor unit.

Gas composition monitoring systems, which can be used to detect metabolic activity of microorganisms are limited to monitoring either oxygen or carbon dioxide. Carbon dioxide sensors can use an acid-base indicator chromophore to modulate the signal output of a fluorophore. In such a system the chromophore absorbance spectrum changes when the pH value of a measured sample changes. The system is able to determine the carbon dioxide level because the pH value of a measured sample depends upon the carbon dioxide level of the sample environment. A monitoring system, which determines metabolic activity of microorgansims by employing an oxygen sensor, can employ an oxygen sensitive fluorophore to detect the oxygen level changes in a sample environment. Prior to the present invention, the combination of the ability to monitor both carbon dioxide and oxygen levels in a gas composition simultaneously was frustrated by the overwhelming problem of cross-talk between the system sensors.

The present invention addresses this problem by providing a sensor formulation and system that can respond independently and simultaneously to oxygen and carbon dioxide.

SUMMARY OF THE INVENTION

It is therefore an object of this invention to provide an improved monitoring system to detect the presence of, and to evaluate the metabolic activity of anerobic or aerobic microorganisms present in a liquid or semi-solid media. It is another object of this invention to provide a microbial monitoring system which can independently and simultaneously monitor oxygen levels and carbon dioxide levels in a gas composition. It is another object of the present invention to provide an improved system that can detect and/or monitor the activity of oxygen consuming enzymes or enzyme systems as well as the effect of growth inhibiting compounds, such as antibiotics on microorganisms. It is another object of the invention to provide a novel formulation for use in monitoring metabolic activity of an organism. It is another object of the invention to provide a means for minimizing the cross-talk between distinct gas component sensors, which are simultaneously monitoring different components of a gas composition. It is another object of the present invention to provide a method of making an improved formulation, which can be used to monitor the metabolic activity of a microorganism by individually and simultaneously detecting levels of oxygen and carbon dioxide in a gas composition. Additionally, it is an object of the present invention to provide a method for monitoring metabolic activity of a microorganism, the method encompassing the use of the monitoring system of the present invention.

The above and related objects are realized by the present invention. The present invention includes the use of a novel fluorescence detection system wherein fluorescing sensor compounds are employed to measurably respond individually and simultaneously to the level of oxygen and the level of carbon dioxide associated with the metabolic activity of a microorganism with minimal or no cross-talk between the different sensor compounds.

The fluorescence system of the present invention can be employed with a modified commercially available fluorescence reading device, such as, but not limited to a breadboard configured from a BD 9050 instrument. The modified florescence reading device can be so modified as to have at least two sensors, each sensor being separately matched to the wavelength of a corresponding fluorophore dye. An example of such a modified fluorescence reading instrument can be the commercially available BD 9050 device that has been modified to have two sensors matched to the respective wavelengths (sensitivity) of two corresponding fluorophore dyes; one of the fluorophore dyes being included in the formulation of the present invention for the purpose of reacting to oxygen levels in the sample being studied and the second fluorophore dye being included in the formulation for the purpose of reacting to the carbon dioxide levels of the sample being tested. It is within the concept of the present invention that, if it is desired to measure additional gases in a gas composition, additional distinct fluorophore dyes corresponding to additional sensors for the additional gases to be monitored can be employed. The additional sensors can be separately and distinctly matched to the respective wavelengths of the additional corresponding fluorophore dyes as necessary.

The sensor formulation of the present invention can be brought into contact with the test sample (either directly or separated by an oxygen permeable membrane) and the level of fluorescence for each of the fluorophore dyes of the composition can be measured using fluorescence reading equipment as described above. An increase in fluorescence is indicative of respiring aerobic microorganisms, which utilize (and thereby reduce) the oxygen in the sample.

The system can, thus, be used to detect a variety of respiring microorganisms, both anerobic and aerobic. It is further anticipated that this system can be used to detect the effectiveness of compounds such as antibiotics on the metabolic activity of microorganisms.

DETAILED DESCRIPTION OF INVENTION

Figure 1:
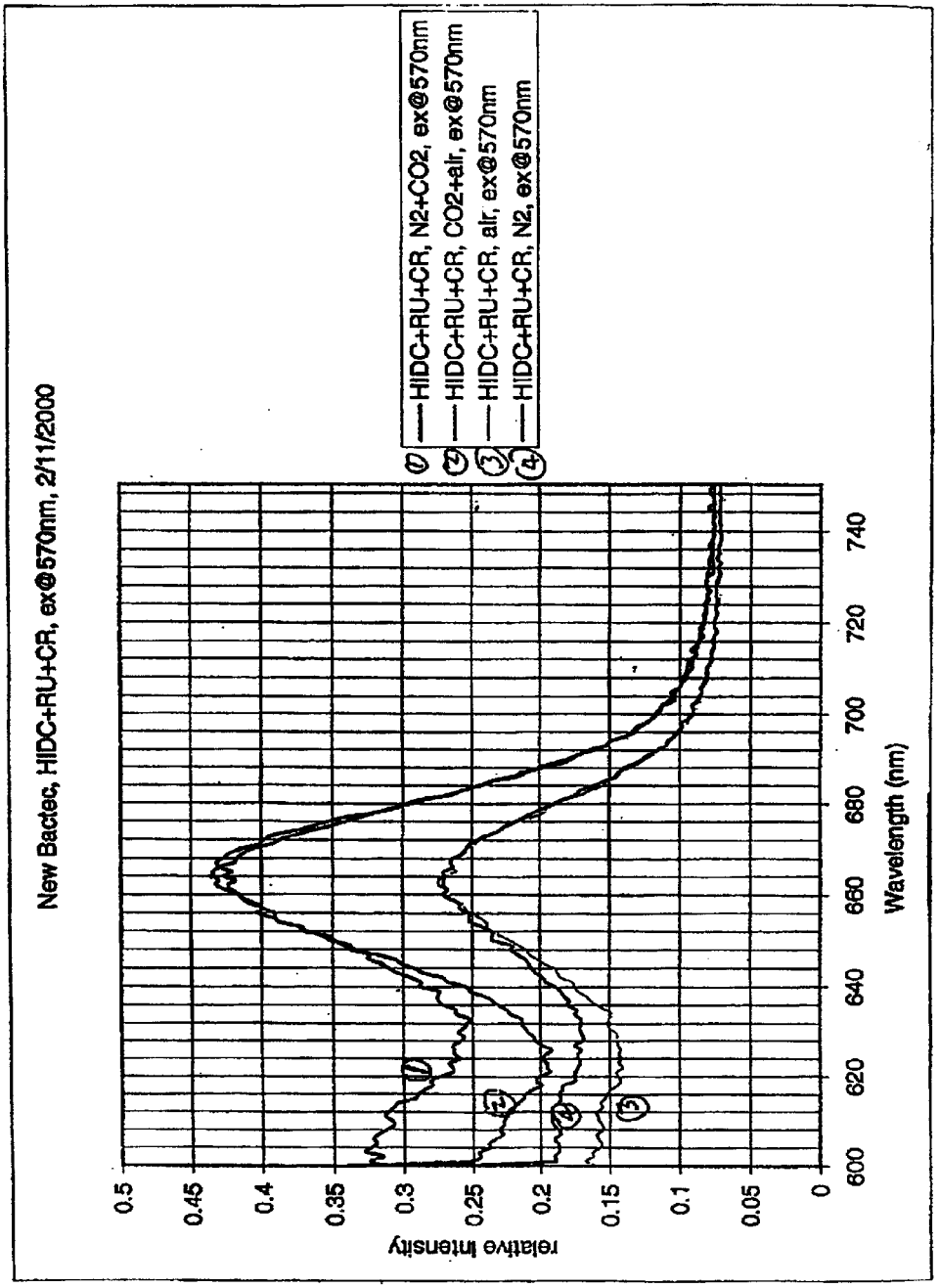
FIG. 1 shows the spectra of the sensor formulation of example 4 at 570 nm. Sensor responses under $N_2$ and $CO_2$, $CO_2$ and air, air alone, and $N_2$ alone are graphically displayed.

The biological sensor system of the present invention provides a novel sensor formulation which when employed in the sensor system is capable of detecting the growth of both anaerobic and aerobic microorganisms in a sample. The unexpected result of simultaneously sensing changes in oxygen and carbon dioxide gas levels in a gas composition with minimal to no cross talk between the distinct sensors for the two gases is achieved due to the novel sensor formulation. The sensor formulation is composed of a mixture of chromophore, fluorophores, and supporting inert materials in such a way that each active fluorophore dye can respond to a specific gas composition change in a distinct manner without cross-interaction with the simultaneous composition changes detected by another fluorophore dye in the same sensor matrix. The sensor system of the present invention achieves this minimization of cross-talk between sensors by employment of the novel sensor composition.

The present invention, therefore, provides a novel formulation of composition for a "combi-sensor" for $CO_2$ and $O_2$ detection-in one sensing element; the method of manufacturing the sensor; and the use of the sensor to detect the growth (or the inhibition of growth as may be the case with anti-biotic drugs) of a large variety of disease causing microorganisms by both $CO_2$ production and $O_2$ consumption. It is also possible to use this sensor to detect the growth (or the inhibition of growth) in eukariotic cells, such as those grown in tissue culture and used for drug screening.

The novel formulation of the present invention allows both $CO_2$ production and $O_2$ consumption to be monitored without the expected cross-talk between sensors. Thus, as the $CO_2$ level of the sample changes the chromophore absorbance spectrum changes. The $CO_2$ sensor employs an acid-base indicator chromophore as a modulator to modulate the signal output of a fluorophore dye. As the $CO_2$ level of the sample environment changes, the pH value correspondingly changes. The chromophore absorbance spectrum changes in relation to the change in pH value. The $O_2$ sensor employs an oxygen sensitive fluorophore dye that correspondingly changes with a change in $O_2$ levels in the sample environment. The sensors in a fluorescence reading device can be tuned to the wavelength of distinct dyes for each of the separate gases being monitored; however, the cross-talk between the different sensors can be so severe as to nullify any effort to monitor the gas composition.

The present invention solves this problem of cross-talk between sensors and provides distinct sensors giving high returns for each of the monitored gases by use of the novel sensor formulation. By way of example of the present invention, any $O_2$ sensitive fluorophore dye can be coated on to a heavier density silica powder. The dense silica powder causes the fluorophore coated silica to settle to the bottom of the sensor matrix as it is formed. The fluorophore dye which is used for $CO_2$ detection is coated on a lighter density silica, which results in the $CO_2$ associated fluorophore being floated throughout the sensor matrix. The acid-base indicator chromophore is made into an emulsion into the sensor matrix and therefore dispersed throughout the sensor matrix. By careful selection of the formulation components, the spectra profile of the $O_2$ sensitive fluorophore and $CO_2$ sensitive fluorophore can have minimum or no overlaps. The $O_2$ signal operates near independently from the $CO_2$ variations due to the segregated configuration of the different sensors, which results from the distinct densities of the selected silica used during matrix formation. Similarly, the $CO_2$ modulation operates near independently from the oxygen level sensor due to the segregated configuration of the formulation described above.

EXAMPLES

The sensor formulation can be composed of a mixture of chromophore, fluorophores, and supporting inert materials A non limiting example of the novel sensor formulation of the present invention can include (a) tris(4,7-diphenyl-10-phenanthroline) ruthenium dichloride pentahydrate; (b) 1.1', 3,3,3',3'-Hexamethylindodicarbobyanine iodide; (c) an acid-base indicator dye; (d) a silicon polymer; (e) a hydrogen-silicon compound; (f) a catalyst; and optionally (g) an inhibitor and a method for preparing the novel composition. Importantly, the selection of components of the novel formulation allows one of ordinary skill in the art to tailor the sensor system to provide a clear gas composition determination for each sample being tested. It is also important to understand that while the examples provided are directed to a sensor formulation and system, which can simultaneously detect $O_2$ and $CO_2$ levels in a gas composition, the formulation and system can be, if desired, expanded to include additional sensors and additional corresponding fluorophore dyes which can enable the simultaneous monitoring of additional gases. The sensor system therefore has a very broad range of capabilities and is not limited to the examples described herein.

Formulations for some non-limiting examples of the sensor composition of the present invention are provided in Table 1. The specific components shown for each of the examples of Table 1 are representative of components which can be selected to achieve the present invention. The novel formulation of the present invention can include any mixture of chromophore, fluorophores, and supporting inert materials which in combination result in a high return of the fluorescent signal for the distinct fluorophore dyes with minimal to no cross talk between the corresponding sensors.

TABLE 1

| Example No. | 1 | 2 | 3 | 4 |
|---|---|---|---|---|
| Components | | | | |
| MCP Stock Sol.[1] | | 0.5 g | | |
| HFCS[2] | 0.3 g | 0.41 g | 0.2 g | 0.2 g |
| Cresol Red[3] | | | | 0.36 g |
| BTB dye[4] | 0.3 g | | 0.3 g | |
| $TiO_2$ | 0.03 g | 0.03 g | 0.3 g | 0.03 g |
| Polymer Part A[5] | 21.0 g | 21.0 g | 21.0 g | 21.0 g |

TABLE 1-continued

| Example No. | 1 | 2 | 3 | 4 |
| --- | --- | --- | --- | --- |
| Polymer Part B[6] | 3.5 g | 3.5 g | 3.5 g | 3.5 g |
| RFCS[7] | | 0.26 g | 0.25 g | 0.25 g |
| 1% Ru/EtoH | 0.2 g | | | |
| Settling time | 3 hr. | 3 hr. | 3 hr. | 3 hr. |
| Time/Temp | overnight/90° C. | Overnight/75° C. | 3.5 hr./75° C. | 3.5 hr./75° C. |

[1]MCP Stock Sol. is 0.19 g m - cresol purple + 4.54 g CAPS + 0.086 g thymolphtalein + 22.14 g 1N NaOH + 78.5 g DI $H_2O$ stock solution.
[2]HFCS is a HIDC Flurophore Coated Silica.
[3]Cresol Red Stock Sol. is 0.345 g Cresol Red + 0.54 g Tricine + 4.95 g 1N NaOH + 0.19 g KCl + 25.2 g DI $H_2O$.
[4]BTB dye is 2.0 g BTB + 28.0 g CAPS + 0.53 g thymolphthalein + 16.0 g 1N NaOH + 0.65 g KCl + 100 g DI $H_2O$.
[5]Polymer Part A is a polydimethylsiloxane; preferably a vinyl dimethyl terminated polydimethylsiloxane.
[6]Polymer Part B is a mixture of polymethylhydrodimethyl siloxane copolymer and a siloxane copolymer.
[7]RFCS is Ruthinium Flurophore Coated Silica.

A modified BD 9050 fluorescence reading device was provided with channel configurations as shown in Table 2. Similar channel configurations can be provided for any fluorescence reading device which one of ordinary skill in the art would use to monitor metabolism of a microorganism

TABLE 2

Channel Configurations (modified BD 9050)

| ID | Channel | EX Filter | EM Filter | LED current (mA) | Feedback Resis ($R_1$ inM) |
| --- | --- | --- | --- | --- | --- |
| NB1314 | A ($O_2$) | 467IF10 | 660IF40 | 20 | 25 |
| | B ($CO_2$) | 573IF12 | 630IF40 | 20 | 10 |

To prepare a 1.1',3,3,3',3'-Hexamethylindodicarbocyanine iodide hereinafter called "HIDC") coated silica, a solution of 0.0715 g of HIDC in 40 g of 95% ethanol was made. The solution was then mixed with 54 g of Degussa Aerosil® R812 Silica (hereinafter called "R812"). The mixture was then air dried and the resulting solid was grinded.

A Cresol Red Indicator stock solution (hereinafter called "CR") was prepared by dissolving 0.345 g of Cresol Red (CAS# 1733-12-6), 0.54 g of Tricine (CAS#5704-04-1) and 0.19 g of KCl in 4.95 g of 1N NaOH and 25.2 g of Deionized water.

A Tris(4,7-diphenyl-1,10 phenanthroline Ruthenium Chloride Pentahydrate) Ruthenium (II) Chloride Hydrate coated silica (hereinafter called "RFCS") was prepared according to the method described in U.S. Pat. No. 5,567, 598, the complete disclosure of which is fully incorporated herein by reference.

A heat curable silicon base polymer was made by mixing a vinyl terminated polydimethylsiloxane with various amounts of catalyst and inhibitor and a crosslinker, which is a polymethylhydrodimethysiloxane copolymer or a mixture of a vinyl terminated polydimethylsiloxane and a polymethylhydrodimethylsiloxane copolymer. The catalyst can be included in the formulation from 1 ppm to 5% and the inhibitor can be included from 1 ppm to 10%. Non-limiting examples of satisfactory catalyst and inhibitor are a platinum catalyst and a cyclic vinylmethyl-dimethylsiloxane inhibitor.

The sensor formulation can consist of 0.36 g of CR, 0.2 g of HIDC coated silica, 0.03 g of DuPont Ti-Pure Titanium Dioxide as light reflectors, and 21 g of polymer. The resulting mixture can be mixed mechanically. RFCS (0.25 g) can be added to the above mixture and mixed again. After the second mixing of the formulation, 3.5 g of a crosslinker can be added and mixed the third time. Any suitable crosslinker can be employed depending upon the degree of cross-linking desired. Two grams of the resulting sensor mixture was loaded into a Bactec 9000 glass bottle. The sensor bottle can then be allowed to set at ambient room temperature for three hours followed by heat cure at 75 degree for 3.5 hours. Variations on this method can be made without departing from the concept of the present invention.

The combination sensor signals are measured by two separate detectors at two different wavelengths of a same instrument unit on a same sensor device. The breadboard used to monitor sensor function in the examples was made from a modified BD 9050 instrument. The instrument was modified so as to match the distinct wavelengths of the dyes/fluorophores in the sensor composition to the instrument. Two detector channels were provided in the modified instrument. One was provided for oxygen variation signals and the second was provided for $CO_2$ variation signals. The wavelength control of any detector can be accomplished by appropriate LED's or filters or the combination of the two. The simplicity of the modifications to any fluorescence reading capable instrument is within the ordinary skill of one familiar with such instruments.

Figure 2:
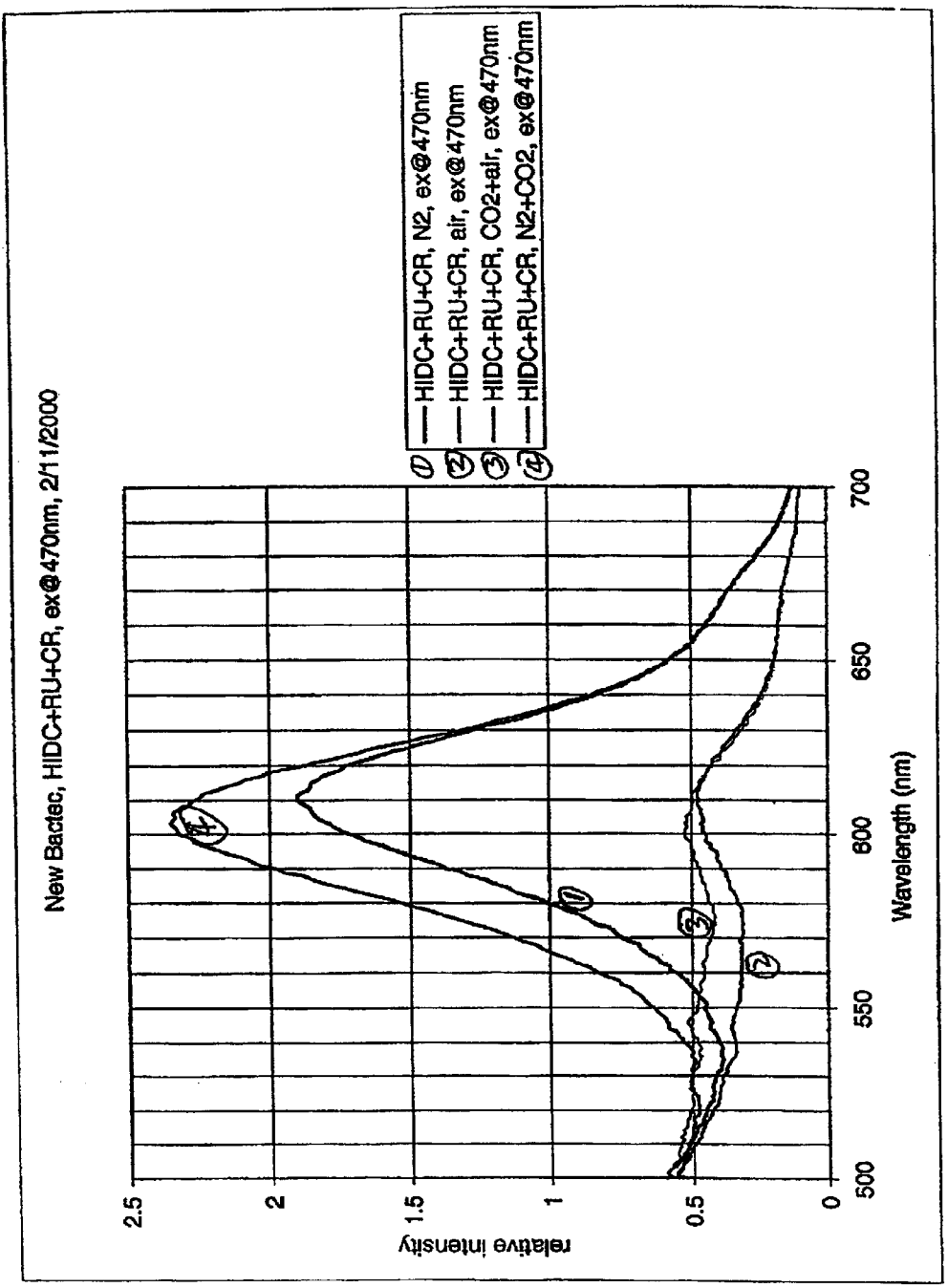
FIG. 2 shows the spectra of the sensor formulation of example 4 at 470 nm. Sensor responses under $N_2$ and $CO_2$, $CO_2$ and air, air alone, and $N_2$ alone are graphically displayed.

Approximately 30 ml of deionized water was added to the sensor formulation and the container was sealed with a butyl rubber septum. The initial signal of the sensor formulation was measured in the modified fluorescence reading device as signals under the category "Air". It was then flushed with nitrogen to obtain the signal measurement under "$N_2$" or oxygen-free environment. The same sensor was then flushed with nitrogen contained 30% $CO_2$ for "30% $CO_2/N_2$ signals. Finally the same sensor was flushed with 30% $CO_2$ balanced with air and the corresponding signals were measured. FIGS. 1 and 2 provide a graphic display of $CO_2$ monitoring of a test sample, example 4. Shown is the spectra of the sensor formulation of example 4 at 570 nm and 470 nm respectively. Sensor responses under $N_2$ and $CO_2$, $CO_2$ and air, air alone, and $N_2$ alone are graphically displayed. Table 2 provides the results of monitoring of examples 1–4 using the same technique described above. It can be seen how one of ordinary skill in the art can control the results of sample monitoring by varying the composition of the sensor formulation.

Signal measurements with a modified BD9050 device under various gas compositions are summarized below with examples including a preferred embodiment, example 4.

The best result was obtained with example 4 which represents a high dynamic range and low cross-talk in both oxygen and carbon dioxide channels. The dynamic range measures the signal change upon gas composition changes. The cross-talk indicates the independency of one gas composition change from the other.

To provide consistency in evaluating the formulations of the present invention, the test material employed for all formulation examples was an artificially prepared gas composition. The prepared gas composition includes 30% $CO_2$ and is a generally accepted gas composition to mimic real microbiology growing profiles. The glass sensor bottle, which contains the artificial gas composition is capped with a rubber septum. A double-needle device is then inserted with one needle connected to a gas supplier and the other needle open to the air. The gas supplier is a gas cylinder with a specific gas composition such as pure nitrogen, 30% $CO_2$ balanced with nitrogen and so on. These gas cylinders can be purchased directly from commercial distributors or customized through the vendors. The specified gas is then flushed through the sensor bottle for an undefined period (normally five minutes) to replace the air with the desired gas. While the gas cylinder is still allowing gas to flow into the sensor bottle, the needle device is pulled out to complete the process.

What is claimed is:

1. A sensor formulation for simultaneously monitoring at least two components of a gas composition, comprising:
   at least two fluorophores;
   an acid-base indicator chromophore dye; and
   a polymeric matrix,
   wherein said chromophore dye and said at least two fluorophores are mixed within said polymeric matrix prior to the polymerization of said matrix.

2. A sensor formulation according to claim 1, wherein a first fluorophore is a fluorophore that responds to changes in the concentration of oxygen in a gas composition and said acid-base indicator chromophore dye responds to changes in the concentration of carbon dioxide in said gas composition to modulate a signal output of a second fluorophore.

3. A sensor formulation according to claim 2, further comprising two different silica powders, said two different silica powders being a first silica powder and a second silica powder; said first silica powder having a greater density as compared to the density of said second silica powder, said first fluorophore being coated on granules of said first silica powder and said second fluorophore being coated on said second silica powder.

4. A sensor formulation according to claim 1, wherein said chromophore dye is evenly dispersed within said polymeric matrix.

5. A sensor formulation according to claim 2, wherein said first fluorophore is segregated from said second fluorophore within said polymeric matrix.

6. A sensor formulation according to claim 1, wherein said polymeric matrix comprises, a first polymer component and a second crosslinker component.

7. A sensor formulation according to claim 6, wherein said first polymer component is a vinyl terminated polydimethylsiloxane and said second crosslinker component is a polymethylhydrodimethylsiloxane copolymer or a mixture of a vinyl terminated polydimethylsiloxane and a polymethylhydrodimethylsiloxane copolymer.

8. A sensor formulation according to claim 6, wherein said polymeric matrix further comprises a catalyst and an inhibitor.

9. A sensor formulation according to claim 8, wherein said catalyst is a platinum catalyst.

10. A sensor formulation according to claim 9, wherein said inhibitor is an inhibitor of said platinum catalyst .

11. A sensor formulation according to claim 10, wherein said inhibitor is cyclic vinylmethyl-dimethylsiloxane.

* * * * *